(12) United States Patent
Hwu et al.

(10) Patent No.: US 10,114,016 B2
(45) Date of Patent: Oct. 30, 2018

(54) PARTICLES AND MANUFACTURING METHODS THEREOF

(75) Inventors: Yeu-Kuang Hwu, Taipei (TW);
Chang-Hai Wang, Taipei (TW);
Chi-Jen Liu, Taipei (TW);
Cheng-Liang Wang, Taipei (TW);
Chi-Hsiung Chen, Taipei (TW);
Chung-Shi Yang, Miaoli (TW);
Hong-Ming Lin, Taipei (TW);
Jung-Ho Je, Pohang (KR); Giorgio Margartondo, Renens (CH)

(73) Assignee: Yeu-Kuang Hwu, Taipei (TW)

( * ) Notice: Subject to any disclaimer, the term of this patent is extended or adjusted under 35 U.S.C. 154(b) by 214 days.

(21) Appl. No.: 12/545,822

(22) Filed: Aug. 22, 2009

(65) Prior Publication Data
US 2010/0248297 A1 Sep. 30, 2010

(30) Foreign Application Priority Data

Mar. 31, 2009 (TW) .................................. 98110627

(51) Int. Cl.
*B22F 9/24* (2006.01)
*G01N 33/543* (2006.01)
(Continued)

(52) U.S. Cl.
CPC ....... *G01N 33/5434* (2013.01); *B22F 1/0022* (2013.01); *B22F 1/0062* (2013.01); *B22F 9/02* (2013.01); *B82Y 30/00* (2013.01); *C01B 13/36* (2013.01); *C01B 33/12* (2013.01); *C01G 49/08* (2013.01); *C09C 1/0081* (2013.01); *C09C 1/04* (2013.01); *C09C 1/309* (2013.01); *C09C 1/3072* (2013.01); *C09C 1/3081* (2013.01); *C09C 1/36* (2013.01); *C09C 1/62* (2013.01); *C09C 3/04* (2013.01); *G01N 33/54346* (2013.01);
(Continued)

(58) Field of Classification Search
USPC .......................................................... 75/345
See application file for complete search history.

(56) References Cited

U.S. PATENT DOCUMENTS 7,998,239 B1 * 8/2011 Nenoff et al. .................. 75/345
2006/0057384 A1 * 3/2006 Simard et al. ................ 428/403
(Continued)

FOREIGN PATENT DOCUMENTS

WO WO-2006/049478 A1 * 5/2006

OTHER PUBLICATIONS

Shukla et al., "Biocompatibility of Gold Nanoparticles and Their Endocytotic Fate Inside the Cellular Compartment: A Microscopic Overview", Langmuir 2005, 21, 10644-10654, Published on Web Sep. 27, 2005, American Chemical Society.
(Continued)

*Primary Examiner* — George Wyszomierski
(74) *Attorney, Agent, or Firm* — Pai Patent & Trademark Law Firm; Chao-Chang David Pai

(57) ABSTRACT

Particles and manufacturing methods thereof are provided. The manufacturing method of the particle includes providing a precursor solution containing a precursor dissolved in a solution, and irradiating the precursor solution with a high energy and high flux radiation beam to convert the precursor to nano-particles. Particles with desired dispersion, shape, and size are manufactured without adding a stabilizer or surfactant to the precursor solution.

9 Claims, 17 Drawing Sheets

(51) Int. Cl.

| | |
|---|---|
| *B22F 1/00* | (2006.01) |
| *B22F 9/02* | (2006.01) |
| *B82Y 30/00* | (2011.01) |
| *C01B 13/36* | (2006.01) |
| *C01B 33/12* | (2006.01) |
| *C01G 49/08* | (2006.01) |
| *C09C 1/00* | (2006.01) |
| *C09C 1/04* | (2006.01) |
| *C09C 1/30* | (2006.01) |
| *C09C 1/36* | (2006.01) |
| *C09C 1/62* | (2006.01) |
| *C09C 3/04* | (2006.01) |

(52) U.S. Cl.
CPC ....... *B22F 2999/00* (2013.01); *C01P 2002/72* (2013.01); *C01P 2002/84* (2013.01); *C01P 2004/03* (2013.01); *C01P 2004/04* (2013.01); *C01P 2004/62* (2013.01); *C01P 2004/64* (2013.01); *C01P 2006/12* (2013.01); *Y10T 428/12181* (2015.01); *Y10T 428/249994* (2015.04); *Y10T 428/2991* (2015.01)

(56) References Cited

U.S. PATENT DOCUMENTS

| | | | |
|---|---|---|---|
| 2007/0044590 A1* | 3/2007 | Shieu et al. | 75/345 |
| 2009/0317289 A1* | 12/2009 | Ito et al. | 420/461 |
| 2010/0150828 A1* | 6/2010 | Chen et al. | 424/1.29 |
| 2010/0196192 A1* | 8/2010 | Liu et al. | 420/463 |

OTHER PUBLICATIONS

Paciotti et al., "Colloidal Gold: A Novel Nanoparticle Vector for Tumor Directed Drug Delivery", Drug Delivery, 11:169-183, 2004, Taylor & Francis Inc.

West et al., "Applications of nanotechnology to biotechnology", Current Opinion in Biotechnology 2000, 11:215-217, Elsevier Science Ltd.

Kawano et al., "Stabilizing of plasmid DNA in vivo by PEG-modified cationic gold nanoparticles and the gene expression assisted with electrical pulses", Journal of Controlled Release 111 (2006) 382-389, Available online Feb. 17, 2006, Elsevier B.V.

Bergen et al., "Gold Nanoparticles as a Versatile Platform for Optimizing Physicochemical Parameters for Targeted Drug Delivery", Macromol. Biosci. 2006, 6, 506-516, WILEY-VCH Verlag GmbH & Co. KGaA, Weinheim.

Belloni et al., "Radiation-induced synthesis of mono- and multi-metallic clusters and nanocolloids", New J. Chem., 1998, pp. 1239-1255.

Gachard et al., "Radiation-induced and chemical formation of gold clusters", New J. Chem., 1998, pp. 1257-1265.

Liu et al., "Microwave Heating for the Preparation of Nanometer Gold Particles", Jpn. J. Appl. Phys. vol. 42 (2003) pp. 4152-4158, Part 1, No. 6B, Jun. 2003, The Japan Society of Applied Physics.

Karadas et al., "X-ray-Induced Production of Gold Nanoparticles on a SiO2/Si System and in a Poly(methyl methacrylate) Matrix", Langmuir 2005, 21, 437-442, Published on Web Dec. 2, 2004, American Chemical Society.

* cited by examiner

US 10,114,016 B2

PARTICLES AND MANUFACTURING METHODS THEREOF

CROSS REFERENCE TO RELATED APPLICATIONS

This Application claims priority of Taiwan Patent Application No. 098110627, filed on Mar. 31, 2009, the entirety of which is incorporated by reference herein.

BACKGROUND OF THE INVENTION

Field of the Invention

The invention relates to a class of methods to prepare particles down to the size of nanometers or less in colloidal solutions, to the products obtained with such methods and to the ingredients used by such methods. The preparation of particles is based on the irradiation of a precursor-containing solution by a beam of high-energy photons (x-rays or gamma rays), or of neutrons, or of protons or of electrons.

Description of the Related Art

Colloidal nanoparticles are utilized as active elements in biosensor, bio-imaging and tumor treatment biomedical applications. Examples of excellent biocompatibility and highly selective agglomeration in cancer cells and tissues of colloidal nanoparticles in medicine applications have been disclosed (Langmuir 21(2005) 10644; Durg Deliv. 11 (2004) 169; Curr. Opin. Biotechnol. 11(2000) 215).

For biomedical applications of colloidal nanoparticles, chemical reduction methods are used to obtain suitable sizes, sufficient colloidal stability and appropriate surface properties for biocompatibility and favorable biological response. Unfortunately, the size of the particles synthesized by chemical reduction methods is normally larger than 30 nm (Durg Deliv. 11 (2004) 169; J. Controlled Release 111 (2006) 382; Macromol. Biosci. 6 (2006) 506).

To obtain smaller particles, some kinds of templates are usually utilized such as porous silica, micelle, and emulsion. However, a tedious procedure to remove the template materials results in serious problem in particle purification. In addition, due to the very low concentration of particles, about 0.25 mM, nanosols must be condensed to reach higher particle concentrations by high speed centrifugation.

To solve these problems, an emitted light without a reducing agent has been disclosed to synthesize particles (New J. Chem. 22 (1998) 1239; New J. Chem. 22 (1998) 1257). However, if a low dose rate of γ-rays (A typical γ-rays source has a dose rate up to 5 Gy per hou) is used, the reactions might need to proceed for several hours, which is not favorable for nanoparticle formation. Additionally, manufacturing yields are very low.

Jpn. J. Appl. Phys. 42 (2003 14240) discloses a method for manufacturing particles using microwave heating. Langmuir 21 (2005 437) disclose a method for manufacturing particles using a conventional X-ray source. However, a hydrophilic polymer must be used as a stabilizer in these methods to prevent the aggregation of particles. Further, due to the low reaction rate, exposure time in excess of 30 hours is needed. Since colloid solutions are thermodynamically instable, prolonged exposure of formed nanoparticles to X-ray radiation is unfavorable and results in temperature increase that eventually destroys colloidal stability.

Thus, a novel method for manufacturing particles is required to circumvent the previously mentioned problems.

BRIEF SUMMARY OF THE INVENTION

The invention provides a method for preparing particles, comprising: providing a precursor solution containing a precursor dissolved in a solution; and irradiating the precursor solution with an ionizing radiation beam with high energy and high flux to convert the precursor to the particle.

The invention further provides a particle prepared by the above method.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

Figure 1A:
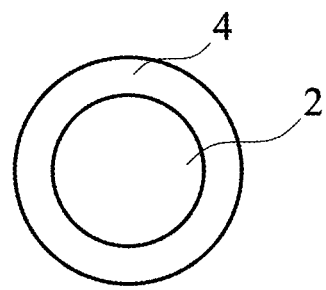
FIGS. 1a-1b show particles of the invention formed on a surface of a granular structure.

The following description is of the best-contemplated mode of carrying out the invention. This description is made for the purpose of illustrating the general principles of the invention and should not be taken in a limiting sense. The scope of the invention is best determined by reference to the appended claims.

The invention provides a method for synthesizing and preparing particles. The method comprises providing a precursor solution containing a precursor dissolved in a solution, and irradiating the precursor solution with an ionizing radiation beam with high energy and high flux to convert the precursor to the particle.

First, a precursor is dissolved in a solution to form a precursor solution, and the precursor solution is reacted by an ionizing radiation beam.

The term "precursor", as used herein, refers to any material which is able to form particles. The precursor of the invention includes, but is not limited to, $AgNO_3$, $HAuCl_4$, $FeCl_2 \cdot 4H_2O$, $NiSO_4^-$, $CuSO_4^-$, or $ZnCl_4$ etc. In one embodiment, in order to form silver particles, $AgNO_3$ can be used as a precursor. In another embodiment, in order to form iron particles, $FeCl_2 \cdot 4H_2O$ can be used as a precursor. The concentration of the precursor is not limited. Generally, the concentration of the precursor is about 0.5 to 2 mM.

The term "solution", as used herein, refers to water, de-ionized water, or alcohol (methanol, ethanol, propyl alcohol, and butanol), but is not limited thereto. One of ordinary skill in the art will select other appropriate solutions, such as, carbon tetrachloride or chloroform.

Next, the precursor solution is exposed by a high energy and high flux radiation beam to convert the precursor to a particle.

The term "high energy and high flux radiation", as used herein, refers to a radiation with a dose rate of more than 0.3 $J/cm^2 sec$. It is noted that if the dose rate is smaller than 0.3 $J/cm^2 sec$, the particle may not be synthesized. Under the irradiation conditions, a large amount of free radicals in the solution which are exposed by the ionizing radiation beam are quickly produced in a short amount of time, wherein the free radicals simultaneously react with all precursors. Thus, the high energy and high flux radiation prevents the aggregation of particles caused by long time exposure of low energy radiation. Examples of radiation include, but are not limited to, X-ray, neutron beam, electron beam, or ion beam. The radiation of the invention includes any radiation which is capable of producing a large number of free radicals for the above mentioned chemical reaction.

The exposure time for the high energy and high flux radiation may be less than 30 minutes, preferably, less than 30 seconds. In one embodiment, the exposure time can be one second. The exposure time of high energy and high flux radiation corresponds to the volume of the precursor solution. The exposure time is increased depending on increasing the volume of the precursor solution. In one embodiment, if the volume of the precursor solution is 10 ml, the exposure time of the high energy and high flux radiation may more than 5 minutes.

Further, before irradiating with the high energy and high flux radiation, poly(ethylene glycol) (PEG), poly(etherimide) (PEI), polyvinyl pyrrolidone (PVP), or isopropylalcohol (IPA) can be added to the precursor solution to increase the stability of the particles. The concentration ratio of PEG, PEI, PVP, or IPA to precursor may be about 0.0001:0.12. The molecular weight of PEG may be between 1000 and 250000.

Moreover, to achieve the best irradiation conditions, the pH level of the precursor solution can be adjusted to 4 to 10 by an NaOH or HCl solution.

In one embodiment, the precursor solution further includes a granular structure. The granular structure of the invention can be a metal or metal oxide, but is not limited thereto. Examples of the granular structure include phosphorous, gold, silver, titanium oxide, zinc oxide, or zirconium oxide. The granular structure can be a commercial product, or be formed by the method for synthesizing particles of the invention.

Figure 1B:
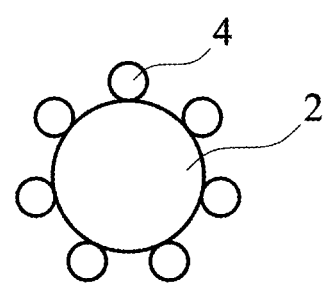

The particle would be formed on the surface of the granular structure, if the precursor solution contains a granular structure. Referring to FIGS. 1a-1b, the particles 2 are completely (FIG. 1a) or partially (FIG. 1b) coated on the surface of the granular structure 4.

Note that it is important for the suitable irradiation intensity. The irradiation intensity of the invention clearly differentiates the present invention with respect to each and all previous investigations, and it is essential for the products quality and therefore for their commercial value with respect to the production costs. The irradiation intensity is specified in terms of dosing rate.

The product (particle) quality refers to the high colloidal density, to the high colloidal stability, and to the chemical purity of the colloidal solution. The commercial value refers, but is not limited, to applications of the products for medical diagnosis and therapy.

The irradiation intensity is a crucial element of the invention for several reasons. First, it increases the production yield thus reducing the production costs. More fundamentally, the methods of the invention are based on the production of free radicals in solution that are unstable; without a suitable irradiation intensity, the production would be simply impossible and not just less expensive. The high intensity is also required for phenomena like the particle charging, underlying the achievement of high colloidal density. Finally, high intensity and therefore fast production avoids significant evolution in time of the solution parameters, to the benefit of uniform particle size and other product characteristics.

In addition to high intensity, the invented methods also require high-energy irradiation allowing production in the entire volume of the precursor-containing solution. For example, the methods can use high-energy photons (x-rays or gamma rays) but not visible photons.

The value of the invention resides on the fact that products with similar quality cannot at present be obtained with other methods. This refers, but is not limited, to the coating of voids inside particles.

In addition to the product quality (stability, concentration and purity), the method of the invention also provides the benefits. The benefits includes: (1) the absence of any pre-added reducing agent or surfactant so that the fabrication process inherently clean and simple for large scale production; (2) the methods do not require templates for particle size control, which simplifies the process; (3) the high intensity irradiation automatically performs sanitization of the products; (4) the irradiation-induced synthesis allows patterning with high precision; (5) the high intensity irradiation induces the required processes for the fabrication in very short exposure times, allowing high production yields and decreasing the costs; (6) the methods allow accurate control of the product characteristics including, but not limited to, the particle size; (7) the methods use water solutions, more biocompatible, simpler to use and less expensive than solutions in oil or other solvents; (8) the chemical reactions can be complete so that chemical purity is obtained without additional processing; (9) the production occurs at room temperature or low temperature, reducing the fabrication costs and avoiding high-temperature damage of the ingredients and products; (10) the entire procedure takes place in only one container even for complex products such as coated particles; (11) the products include not only particles with coated outside surfaces but also particles with controlled filling of the internal voids; (12) the product characteristics are uniform; this specifically refers, but is not limited, to the particle size distribution and to the particle coating, and (13) the methods can be applied to complex chemical reactions to obtain products with versatile characteristics.

In contrast to the conventional method, the method of the invention provides advantages including: (a) having a one-pot reaction without a reducing agent; (b) a pure reactant and product with no need for a surfactant and product side-product; (c) no free radical scavenger, such as 2-propyl alcohol, is required; (d) a short reaction time at room temperature; (e) a colloidal containing particles with high concentrations by large scale manufacturing process; (f) maintenance of superior dispersion, shape, and size of the particles, with recovery rate of about 80%, due to easy concentration of the particles by a centrifugation at 4000. In contrast, the particles synthesized by the conventional method have to be concentrated by a centrifugation at 10000 rpm; (g) superior in vivo stability of the particles; and (h) applicability to synthesize particles from various materials.

Further, the invention also provides a particle colloidal, comprising a solution and a plurality of particles dispersed in the solution. The particle colloidal may not contain a surfactant or stabilizer.

The particle colloidal can be concentrated by a centrifugation to obtain a concentrated liquid, and the concentrated liquid can be further diluted to a solution. In the repeated concentration and dilatation process, the size of the particles is consistent.

The material of the particle of the invention is not limited. In one embodiment, the material of the invention may be a metal, such as gold, silver, nickel, platinum, iron, titanium, zinc, zirconium, or tungsten. In another embodiment, the material of the invention may be a metal oxide, such as iron oxide, nickel oxide, silicon oxide, zinc oxide, zirconium oxide, cerium oxide, tungsten oxide, titanium oxide, or copper oxide, The surface of the particle of the invention can be coated with PEG, PEI, PVP, or IPA, etc.

The particle of the invention can be formed on a surface of a granular structure or a substrate. The granular structure or substrate can be a metal or metal oxide, but is not limited thereto. For example, the particle can be completely or partially formed on the surface of the granular structure. In another embodiment, the granular structure has internal voids, and the particle is partially or completely formed in internal voids of the granular structure. The granular structure with internal voids may be a porous silicon oxide or carbon nanotube.

The particle of the invention can be a nanoparticle. The size of the particle of the invention is not limited, preferably, about 15±5 nm, and the particle of the invention has superior dispersion, shape, and size.

EXAMPLE

Example 1: Synthesis of Silver Particle

Silver (Ag) particles were synthesized from aqueous silver nitrate solutions ($AgNO_3$, 0.1 N, Acros Organics Inc. N.J. US.) by synchrotron x-ray irradiation. Silver nitrate was dissolved in de-ionized water (18.2 MΩ cm, Millipore, Milli-Q, MA, U.S.), and the pH value of the silver nitrate solution was adjusted using a NaOH solution to achieve desired irradiation conditions. 0.5, 1, or 2 mM of silver nitrate solution was added to the polypropylene conical tubes of different sizes (2, 15 ml, Falcon®, Becton Dickinson, N. J. US), and then exposed to a Bl01A beam line. The experiments were performed at the BL01A beam line of the NSRRC (National Synchrotron Radiation Research Center) storage rings (Margaritondo G, Hwu Y and Je J H 2004 Rivista del Nuovo Cimento 27 7). The photons energy distribution was centered between 10 and 15 keV and the dose rate was 5.1±0.9 kGy/sec as determined by a Fricke dosimeter with an estimated G value of 13. Detailed descriptions of the experimental system have been described in Kim C C, Wang C H, Yang Y C, Hwu Y, Seol S K, Kwon Y B, Chen C H, Liou H W, Lin H M, Margaritondo G and Je J H 2006 Mater Chem. Phys. 100 292; Yang Y C, Wang C H, Hwu and Y, Je J H 2006 Mater Chem. Phys. 100 72; Wang C H, Hua T E, Chien C C, Yu Y L, Yang T Y, Liu C J, Leng W H, Hwu Y, Yang Y C, Kim C C, Je J H, Chen C H, Lin H M and Margaritondo G. 2007 Mater Chem. Phys. 106 323; and Wang C H, Chien C H, Yu Y L, Liu C J, Lee C F, Chen C H, Hwu Y, Yang C H, Je J H and Margaritondo G. 2007 J. Synchrotron Radiation 14 477. Unmonochromatized ("pink") x-ray beams with no optical elements except one set of beryllium and Kepton windows was used in this Example. A slit system was used to obtain a transversal beam section of 13×10 $mm^2$. The exposure time ranged from 1 sec to 3 min.

Before irradiation of X ray, PEG (MW 6000, Showa Inc., Japan), PVP (MW 10000, Tokyo Chemical Industry Co., Ltd. Japan) or isopropanol (Mallinckrodt Baker Inc. N.J., US) was added to the silver nitrate solution to improve colloidal stability, size distribution, and biocompatibility. In addition, conventional citrate-reduced silver nanoparticles (citrate-Ag) were also prepared as a control group.

The resulting Ag nanosols of the invention were determined to have been stable for over one year in an ambient environment. On the contrary, the reference silver nanoparticle solutions prepared by citrate reduction (and no irradiation) tended to flocculate and precipitate before one year.

Figure 2:
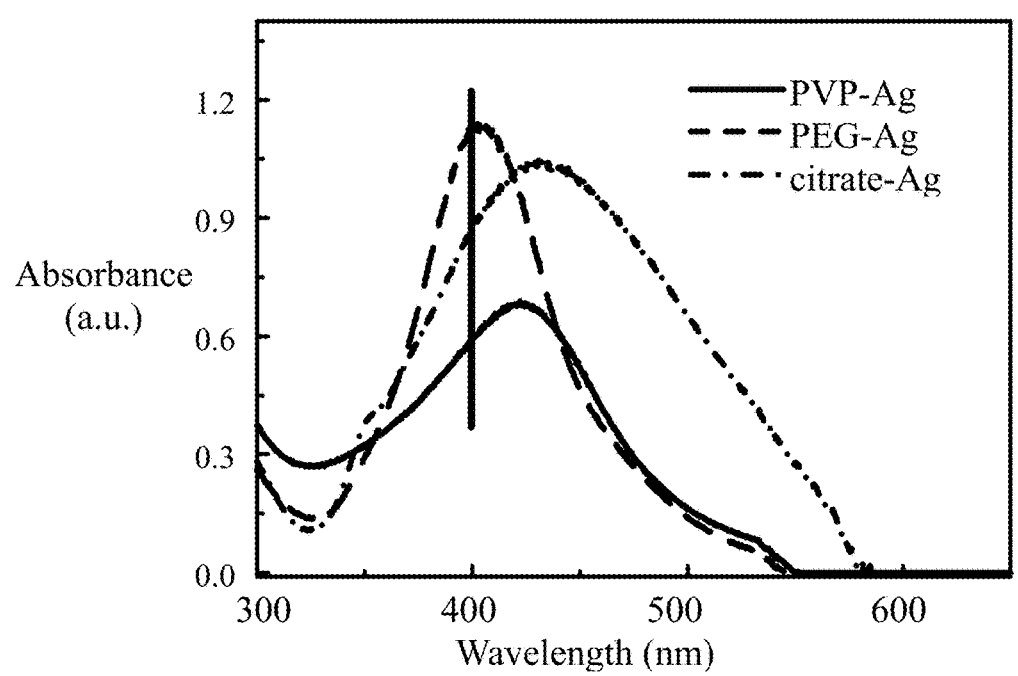
FIG. 2 shows UV-VIS absorption spectra of Ag particles.

FIG. 2 illustrates UV-VIS absorption spectra of Ag nanoparticles (5× diluted to avoid saturation) prepared by X-ray irradiation in the presence of PEG or PVP, or citrate reduction without polymers. For X-ray irradiation, $AgNO_3$ was 0.5 mM, irradiation time was 5 min, PEG was 0.3 mM, and PVP was 0.12 mM. For citrate reduction, $AgNO_3$ was 0.833 mM, and citrate was 6.47 mM.

Referring to FIG. 2, the surface plasmon resonance (SPR) peak position of Ag particle was 404 nm, 422 nm, or 432 nm and the full width at half maximum (FWHM) was 83 nm, 113 nm or 149 nm for PEG-Ag, PVP-Ag and citrate-Ag particles, respectively. Compared to the PEG-Ag nanosols produced by X-ray irradiation, the absorption peak of the citrate-reduced Ag nanosol exhibited a large red-shift of 28 nm and significant flocculation.

Example 2: Effect of X-Ray Exposure Time

Figure 3A:
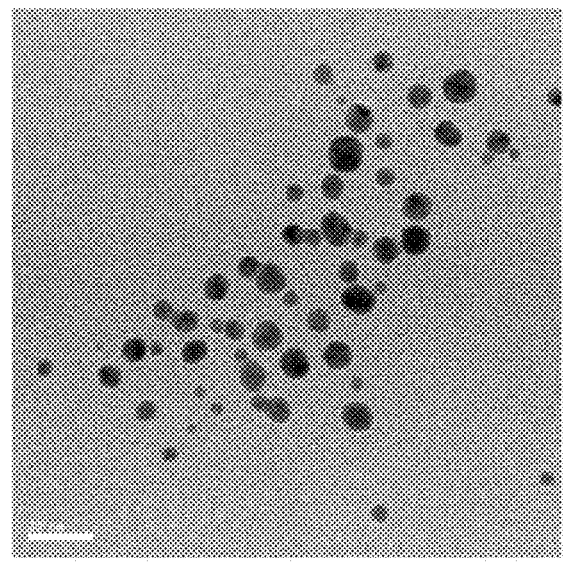
FIGS. 3a-3j show TEM images and corresponding size histograms of Ag particles.
Figure 3B:
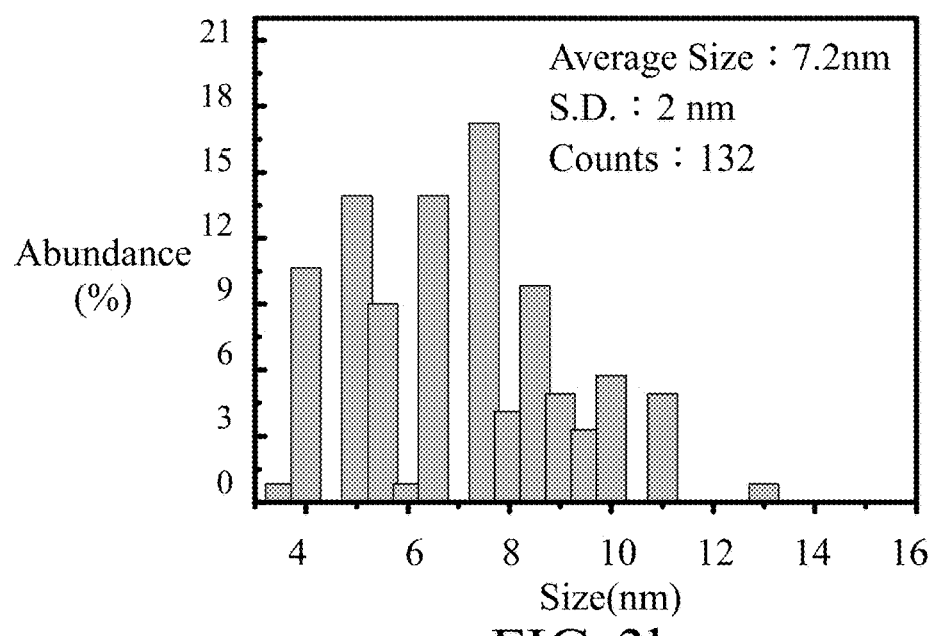
Figure 3C:
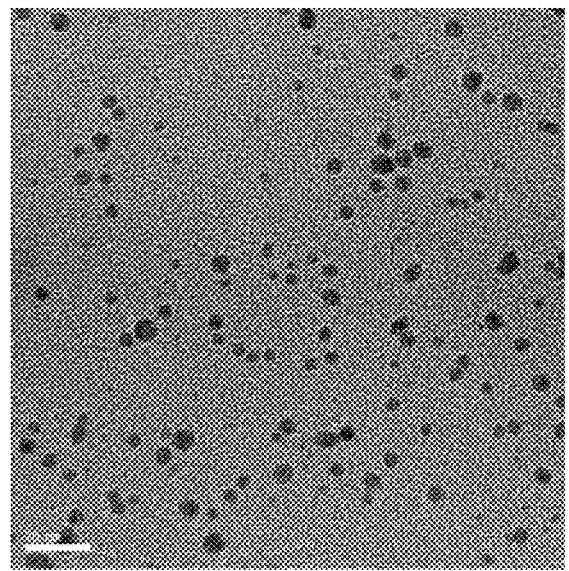
Figure 3D:
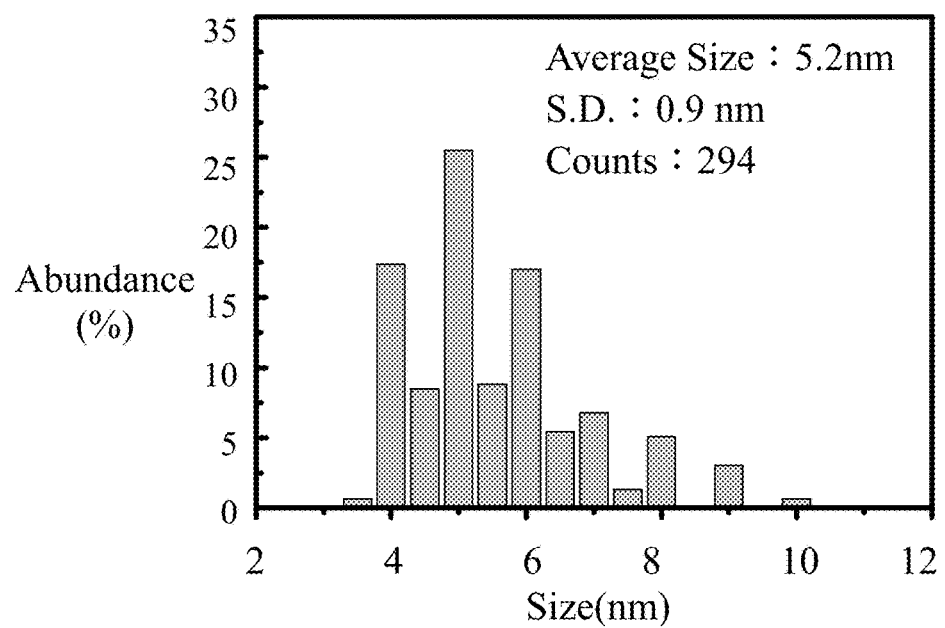
Figure 3E:
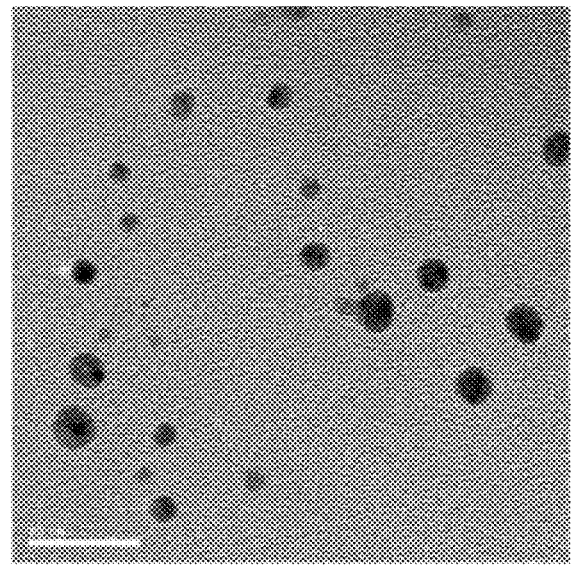
Figure 3F:
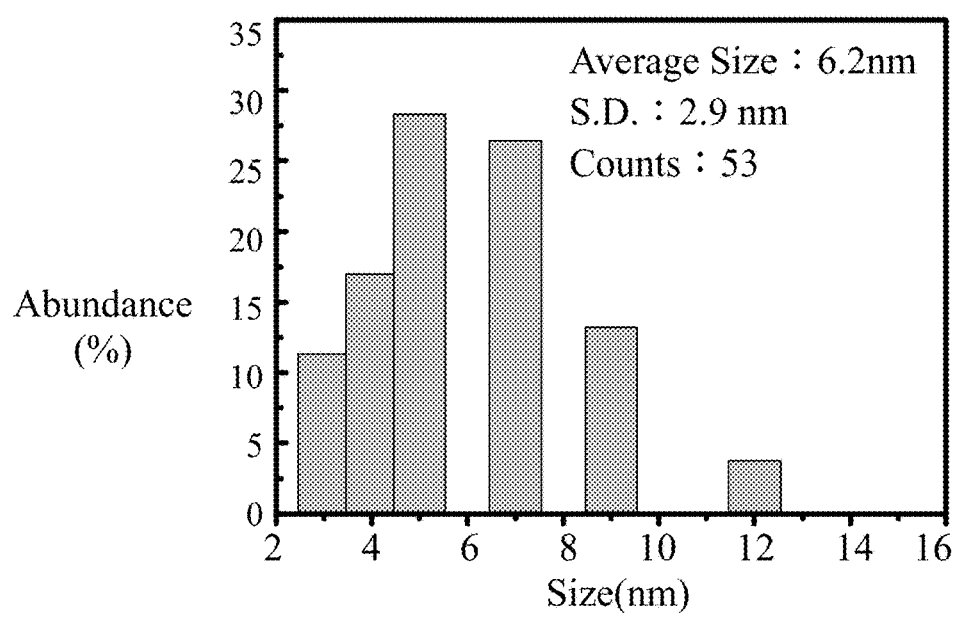
Figure 3G:
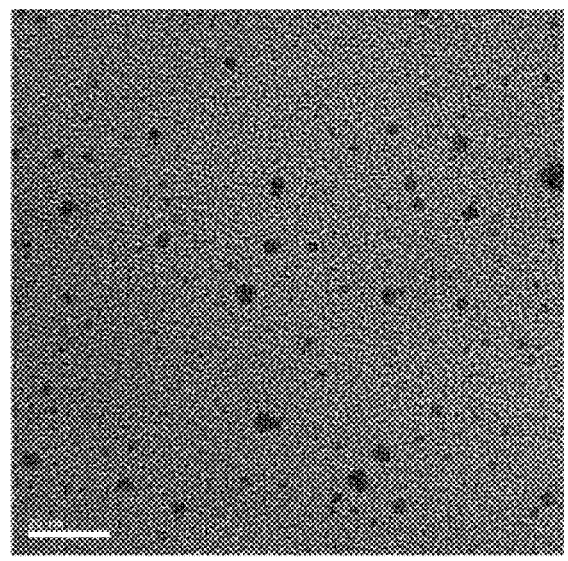
Figure 3H:
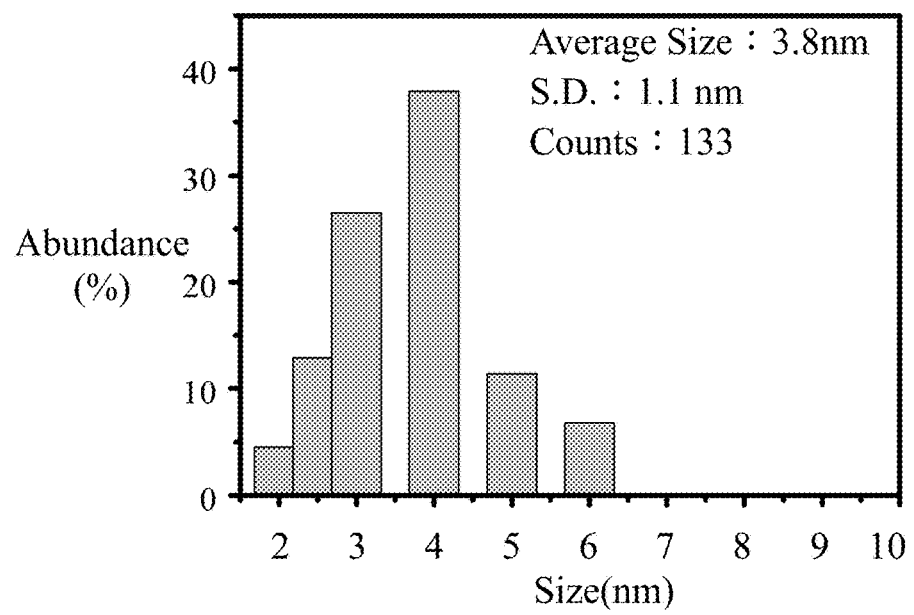

The influence of the irradiation time on the structure and optical absorption spectra of Ag particles prepared by Example 1 was investigated. FIGS. 3a and 3c show TEM results for Ag nanosols prepared in the presence of PEG for 5 seconds and 5 minutes exposure, respectively. FIGS. 3b and 3d show the corresponding size histograms of PEG-Ag particles. The size of PEG-Ag particles was 7.2±2 nm for 5 seconds exposure and the size distribution was broad. After 5 minutes of exposure, the size of PEG-Ag particles was 5.2±0.9 nm and the distribution was narrow. Equivalent results were obtained under similar experimental conditions for the PVP-Ag particles. Referring to FIGS. 3e to 3h, the size of PVP-Ag particles was 6.2±2.9 nm (5 second exposure) and 3.8±1.1 nm (5 minute exposure).

Figure 3I:
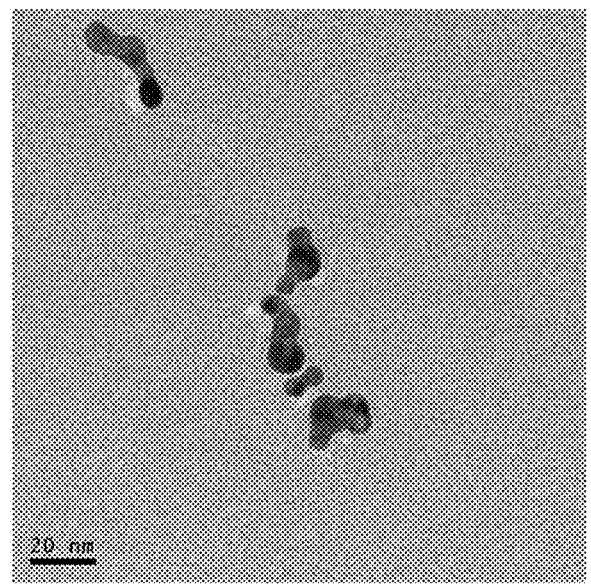
Figure 3J:
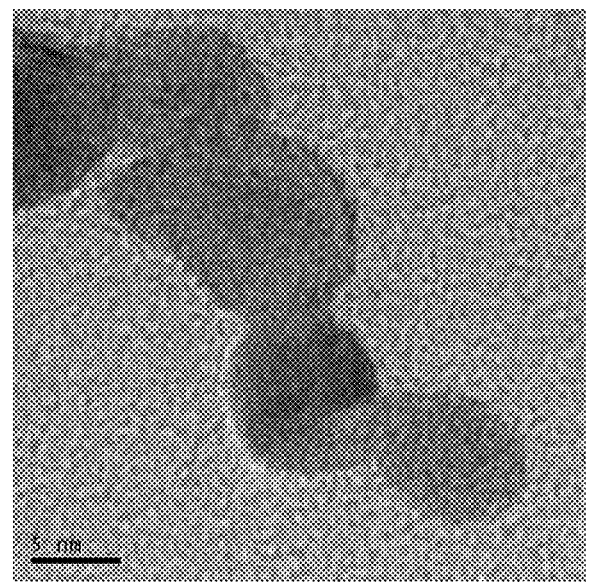

FIGS. 3i to 3j show the size histograms of Au particles synthesized from hydrogen tetrachloroaurate solution ($HAuCl_4.3H_2O$) by the method of Example 1. After 1 second exposure of X-ray, the size of the gold particle was smaller than 10 nm. The results indicate that particles of the invention were stably synthesized by a short 1 second exposure time.

Example 3: Synthesis of Ni—P Metal Colloidal

The Ni—P colloidal was also well synthesized by the method of Example 1. The Ni base structure could be applied in diverse fields such as the electronics, medical, aerospace, automobile, oil, and gas industries since they exhibit excellent resistance to corrosion, oxidation, and wear.

Figure 4:
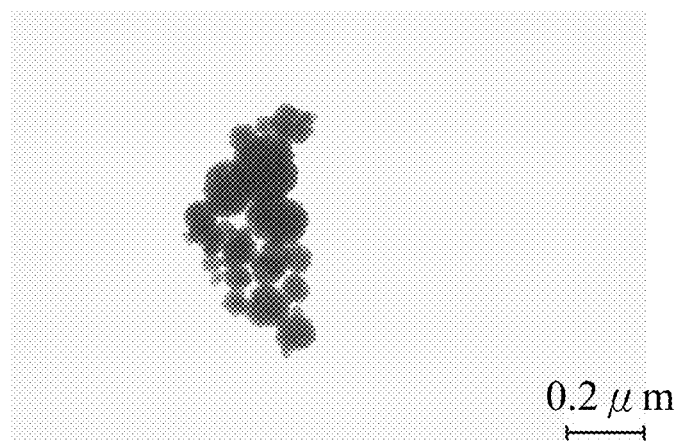
FIG. 4 shows a TEM image of Ni—P particles.

The plating bath consisted of 26 g l$^{-1}$ nickel sulfate, 30 g l$^{-1}$ sodium hypophosphite, 20 g l$^{-1}$ ammonium chloride, and 30 g l$^{-1}$ sodium acetate. Sodium hypophosphite was used as a reduction agent and sodium acetate was used as a complexing agent. The pH level of the solution was adjusted to 4, 5, 6, 7, and 8 by diluted HCl and NaOH solutions, respectively. FIG. 4 shows TEM results for Ni—P nanosols for a 1 minute exposure, wherein the particle size was smaller than 200 nm.

Example 4: Synthesis of Iron Oxide Colloidal

Iron oxide ($Fe_3O_4$ ferrifluid, SDCIO) particles were synthesized from aqueous iron chloride ($FeCl_2.4H_2O$) solutions by the method of Example 1. To achieve the best irradiation conditions, the pH level of the iron chloride solution was adjusted by adding an $NH_4OH$ solution. The exposure time was set at 5 minutes for each 10 ml of the iron chloride solution.

Figure 5:
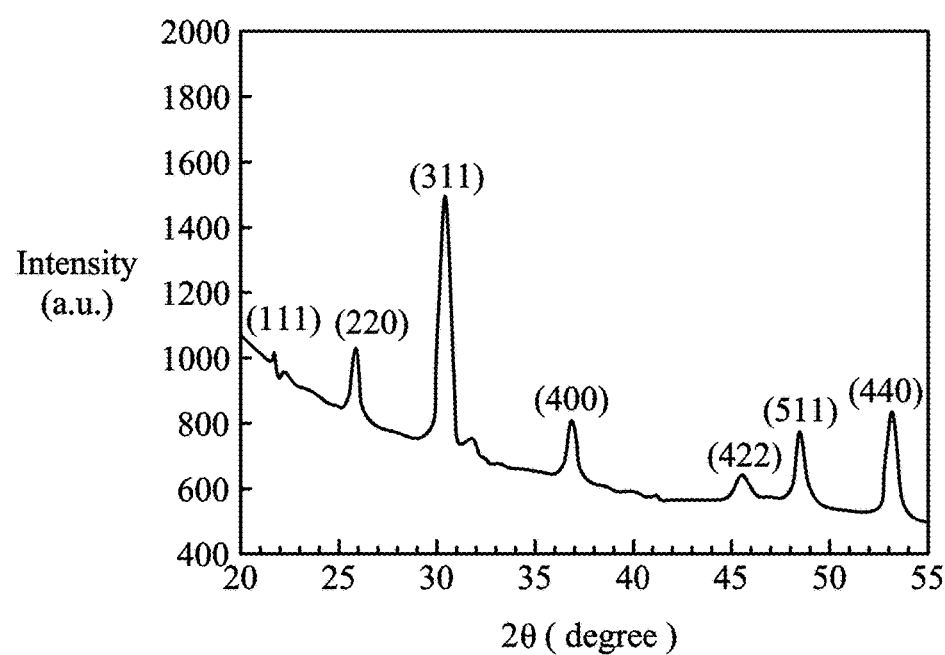
FIG. 5 shows X-ray diffraction of $Fe_3O_4$ particles.
Figure 6A:
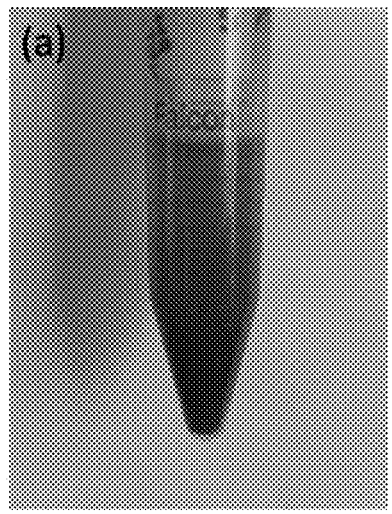
FIGS. 6a-6d show images of direct observation of $Fe_3O_4$ particles obtained at different concentrations of dextran.
Figure 6B:
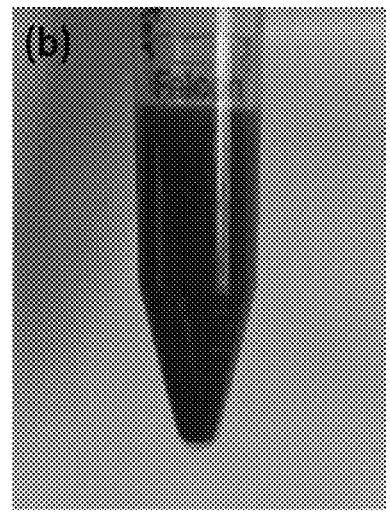
Figure 6C:
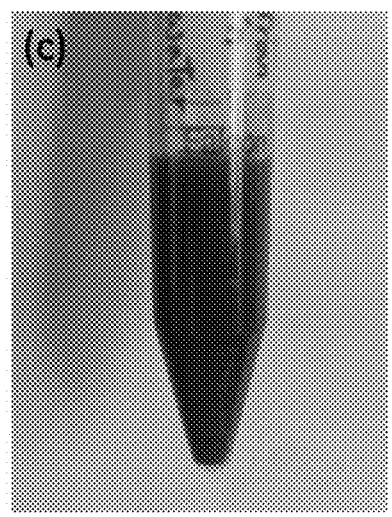
Figure 6D:
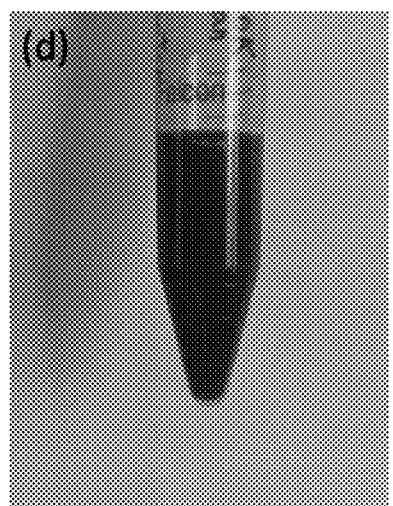

FIG. 5 is an XRD results and it demonstrated the desired structure and phase purity of the $Fe_3O_4$ particles. FIG. 5 shows six peaks including at $2\theta$=25.8, 30.4, 36.9, 45.6, 48.6 and 53.1, which are characteristic diffraction peaks of the $Fe_3O_4$. The peaks corresponded to the three d-spacings (220), (311), (400), (422), 511), and (440), respectively. The average particle size was also derived from the most intense peak, corresponding to the (311) reflection in $Fe_3O_4$, obtaining 12.4 nm according to the Scherrer's equation.

In addition, to improve the colloidal stability of $Fe_3O_4$ colloidal, dextran was added to the iron chloride solution before synchrotron X-ray irradiation. Direction observations of $Fe_3O_4$ nanosols obtained from the iron chloride solutions on different dextran concentrations are shown in FIG. 6, wherein the FIGS. 6a to 6d show $Fe_3O_4$ nanosols with 5%, 10%, 20%, and 50% of dextran, respectively. Referring to FIG. 6, the colloidal stability of $Fe_3O_4$ solution was increased significantly depending on the increase of dextran concentration, and the $Fe_3O_4$ solution could be in the form of ferrifluid in dextran (molecular weight: 10 kDa).

Figure 7:
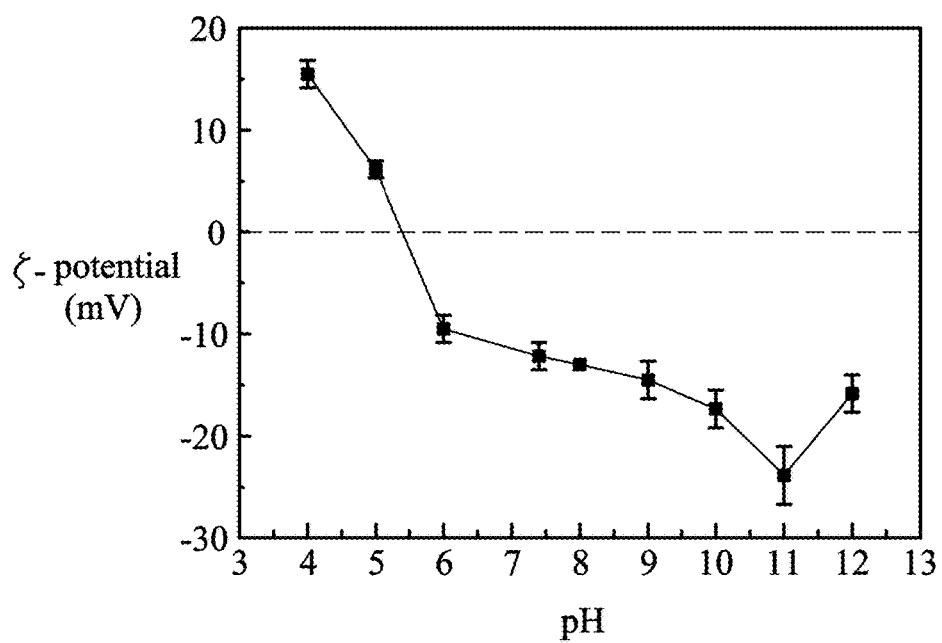
FIG. 7 shows ξ-potential of a dextran-coated $Fe_3O_4$ particle.

Referring to FIG. 7, the ξ-potential as a function of pH on dextran-coated iron oxide nanosols was analyzed. Under the pH 7.4, dextran-coated iron oxide had a negative charge. After increasing the pH value, the 4-potential was decreased, and it indicated that the colloidal stability could be improved by increasing the pH level.

Example 5: Synthesis of Au/$TiO_2$ Composites Colloidal

The photocatalytic efficiency of specific metal oxide, such as $TiO_2$, ZnO, or $ZrO_2$ is an important performance factor for practical applications in areas such as solar cells, sanitization and cancer therapy. Thus, efficiency can be improved by adding Au to a surface thereof. Gold (Au) is particularly interesting because of its biocompatibility and its enhancements of the radiation response. The surfaces of both oxide and of the metal particles must be optimized to achieve maximum efficiency.

0.01 g of commercial P25 $TiO_2$ (anatase phase, specific surface area 50±15 m$^2$/g, average primary particle size 21±3 nm, purity >99.5%) were added to 10 ml of de-ionized water to prepare a well mixed $TiO_2$ nanosol. A mixed aqueous solution containing 0.02 M of gold precursor (hydrogen tetrachloroaurate trihydrate, HAuCl$_4$*3H$_2$O, Aldrich) with an appropriate amount of NaOH (0.1 M) was subsequently added while stirring. The resulting solution was then exposed to high flux of X-ray photons at the BL01A beam line to form the Au/$TiO_2$ particles. The synthesis of Au/$TiO_2$ particles was the same as Example 1.

Figure 8:
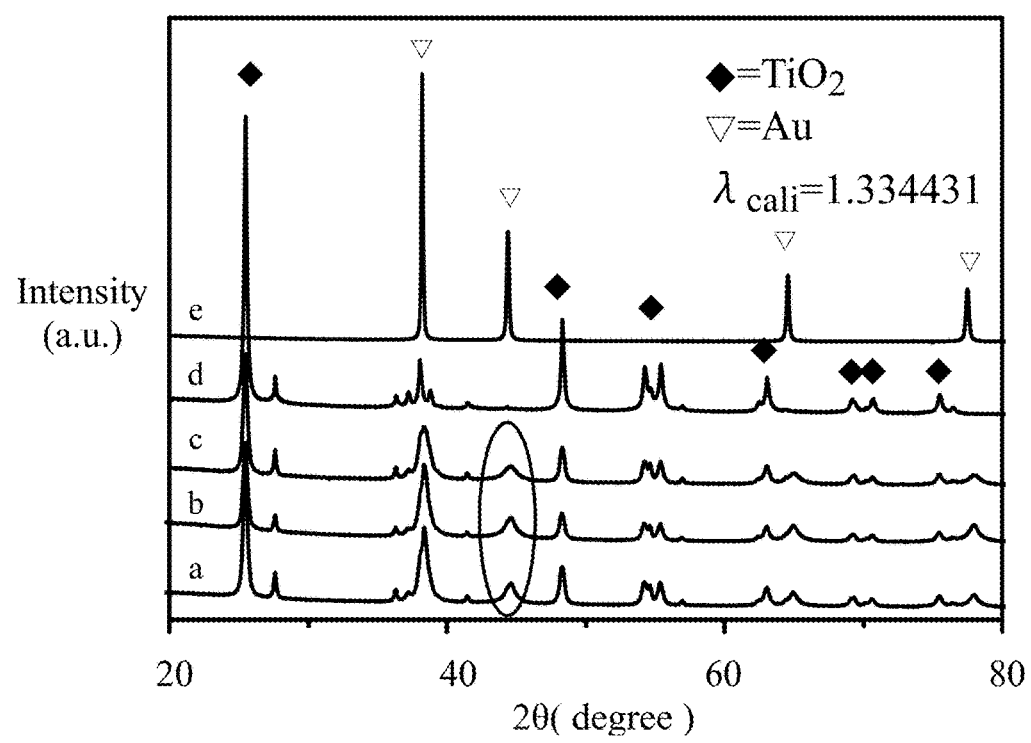
FIG. 8 shows X-ray diffraction of Au, $TiO_2$, and Au/$TiO_2$ particles.
Figure 9A:
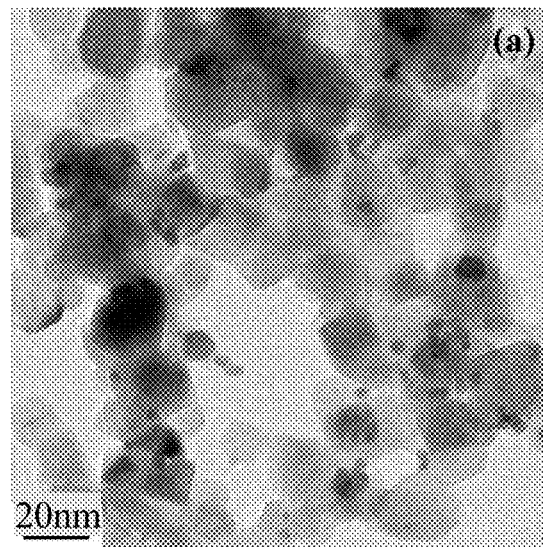
FIGS. 9a-9d show TEM images of Au/$TiO_2$ particles.
Figure 9B:
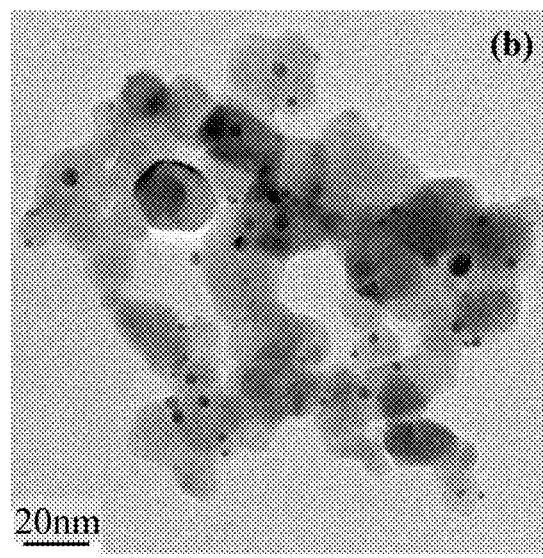
Figure 9C:
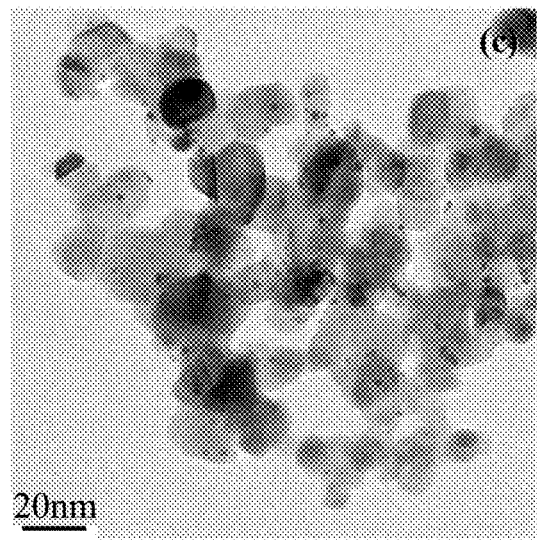
Figure 9D:
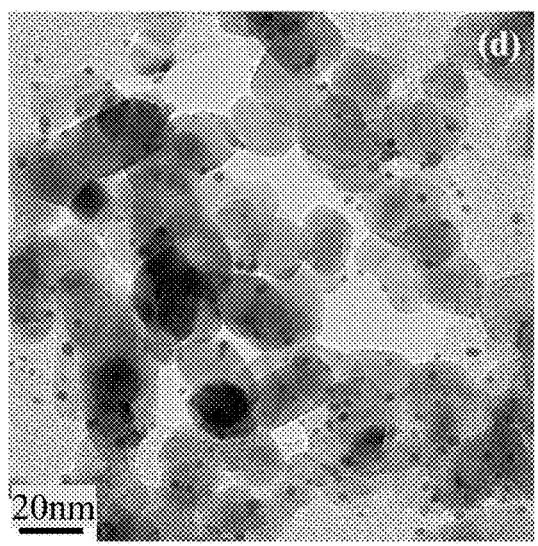

FIG. 8 shows XRD results of the Au, $TiO_2$, and Au/$TiO_2$ particles, which include SP-XRD diffraction patterns of synthesized Au/$TiO_2$ particles for different x-ray exposure times: (a) 5 minutes, (b) 10 minutes, (c) 15 minutes as well as (d) of anatase $TiO_2$ particles and (e) of pure Au particles.

Referring to FIG. 8, the XRD results demonstrated the desired structure and phase purity of the Au, $TiO_2$, and Au/$TiO_2$ particles. The average size of Au particle was derived from the broadening of the Au (111) reflection peak, obtaining 1.11, 0.98 and 0.83 nm according to the Scherrer's equation for different Au/$TiO_2$ samples after 5, 10, and 15 minutes of X-ray exposure. The particle size was decreased depending on an increasing exposure time.

Further, TEM analysis was also used to confirm the size distribution and morphology of the Au particles. FIG. 9 shows a typical set of TEM images of Au/$TiO_2$ particles after drying in solution, wherein the FIGS. 9a-9d illustrate the Au/$TiO_2$ synthesized by X-ray exposure of 1, 5, 10, and 15 minutes, respectively. Referring to FIGS. 9(a)-9(d), the Au particles were uniformly formed on the $TiO_2$ surface. In contrast, shorter x-ray exposure time (e.g., 1 minutes and 3 minutes of FIGS. 3a and 3b) resulted in larger gold nanoparticles than longer x-ray exposure time (e.g., 10 minutes and 15 minutes of FIGS. 3c and 3d). This result was consistent with the XRD results. The size of the Au particles was estimated to be around 2-5 nm depending on the x-ray exposure time. For example, according to the TEM images, the size of the Au particles for an x-ray exposure time of 1 minute was 4.58±1.06 nm, while that for 15 minutes was 2.59±0.88 nm. Au nanoparticles in this range were reported to exhibit high catalytic activity.

Figure 10:
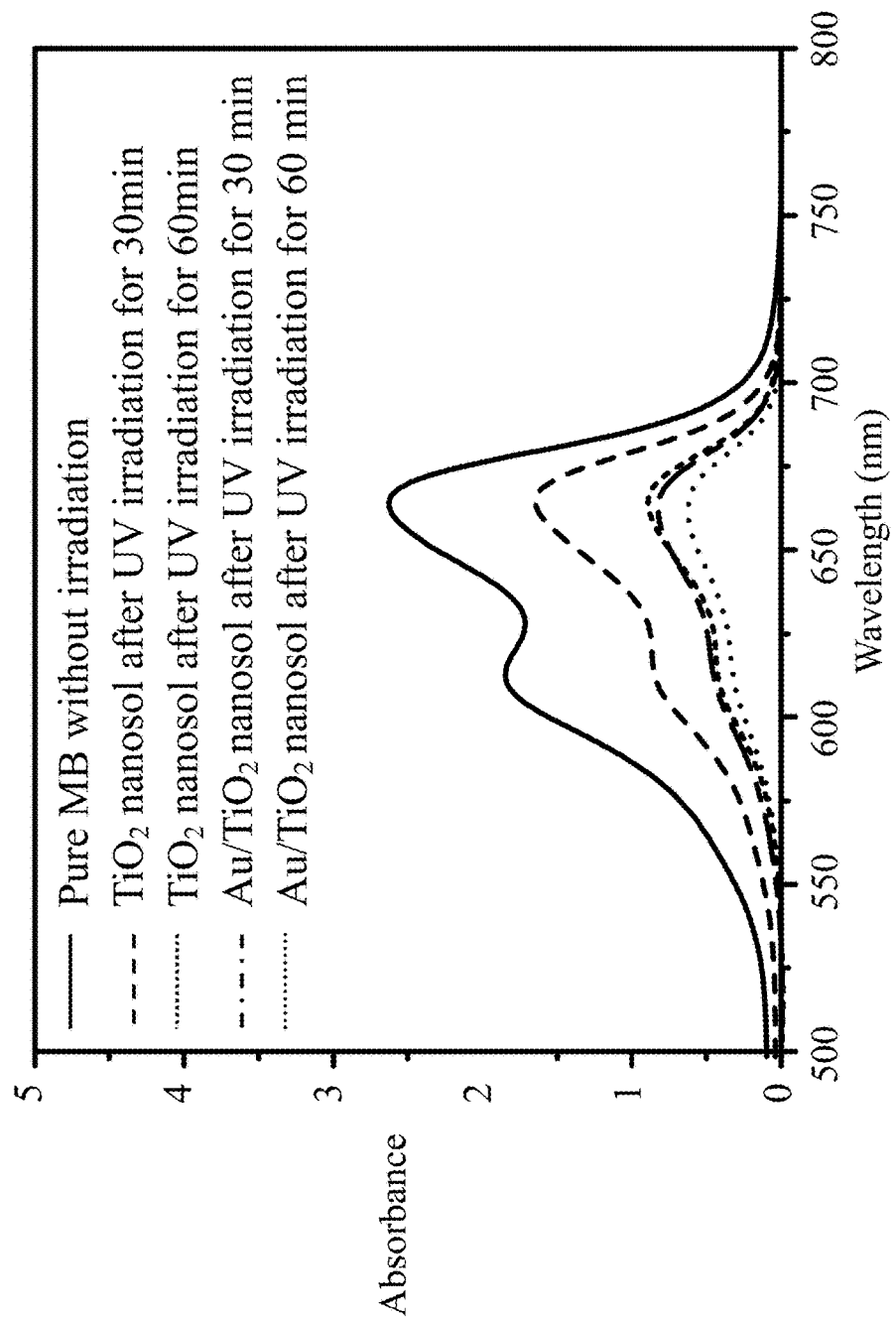
FIG. 10. shows visible light methyl blue (MB) spectral changes in de-ionized water in the presence of $TiO_2$ or Au/$TiO_2$ particles.

FIG. 10 shows visible light methyl blue (MB) spectral changes in de-ionized water in the presence of $TiO_2$ nanosol or x-ray synthesized Au/$TiO_2$ nanosol (the initial concentration was $TiO_2$=0.5 mM; Au/$TiO_2$=0.028 mM/0.5 mM) after UV irradiation with a wavelength of 254 nm for 30 and 60 minutes. Referring to FIG. 10, the decrease in the absorbance at 664 nm reflected the MB degradation resulting from the photon-induced decomposition effect and can be used to evaluate the photocatalytic activity. The results indicated that Au/$TiO_2$ nanosols strongly enhanced the photocatalytic MB decomposition compared to pure $TiO_2$.

The hydrodynamic size of $TiO_2$ and Au/$TiO_2$ nanosols in the RPMI medium or de-ionized water was monitored during 4 hours by dynamic light scattering and the results are summarized in Table 1.

For suspensions in distilled water, the initial average hydrodynamic size of the Au/$TiO_2$ nanosol was 225.3 nm, which is almost the same as that of the $TiO_2$ nanosol (239.1 nm). However, while the $TiO_2$ particles incubated for up to 4 hours, their average hydrodynamic size increased to approximately 342.5 nm. On the contrary, no such increase was observed for Au/$TiO_2$ nanoparticles with average sizes almost unchanged (246.2 nm).

For suspensions in cell culture medium, the initial average hydrodynamic size of $TiO_2$ and Au/$TiO_2$ particles (487.2 and 318.7) was large compared to distilled water. During incubation for up to 4 hours, the $TiO_2$ particle size increased significantly to 635.1 nm, whereas the growth was more limited for Au/$TiO_2$ particles (341 nm). All the results indicated that the colloidal stability of Au/$TiO_2$ nanosol was much better than pure $TiO_2$ nanosol both in distilled water and in the cell culture medium. The size increase of particles in the cell culture medium may be explained by protein absorption.

TABLE 1

| Treatment time | Average size (nm) | |
| --- | --- | --- |
| | 0 hour | 4 hours |
| $TiO_2$ in DI water | 225.3 | 342.5 |
| $TiO_2$ in medium | 487.2 | 635.1 |
| $Au/TiO_2$ in DI water | 239.1 | 246.2 |
| $Au/TiO_2$ in medium | 318.1 | 341 |

DI: de-ionized water

Treatment condition: MB=0.25 mM; $TiO_2$=0.5 mM; $Au/TiO_2$=0.028 mM/0.5 mM

Example 6: Synthesis of Au/ZnO, $AuZrO_2$ Composites Colloidal $Au/TiO_2$, Au/ZnO and $AuZrO_2$ were synthesized by synchrotron X-ray irradiation as mentioned in Example 5.

Figure 11A:
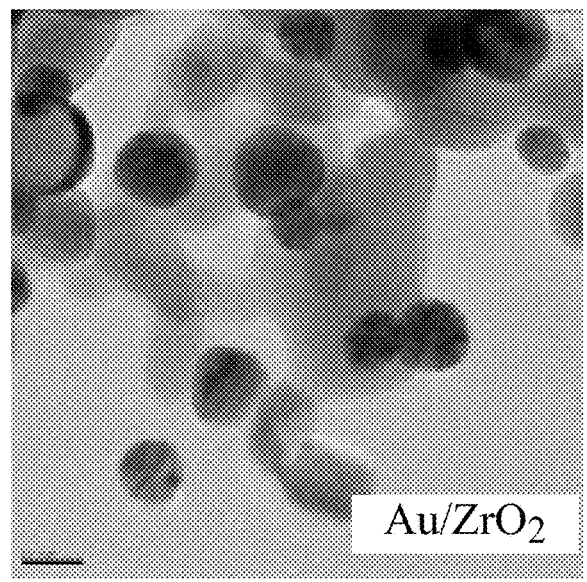
FIGS. 11a-11b show TEM images of Au/ZnO and Au/$ZrO_2$ particles.
Figure 11B:
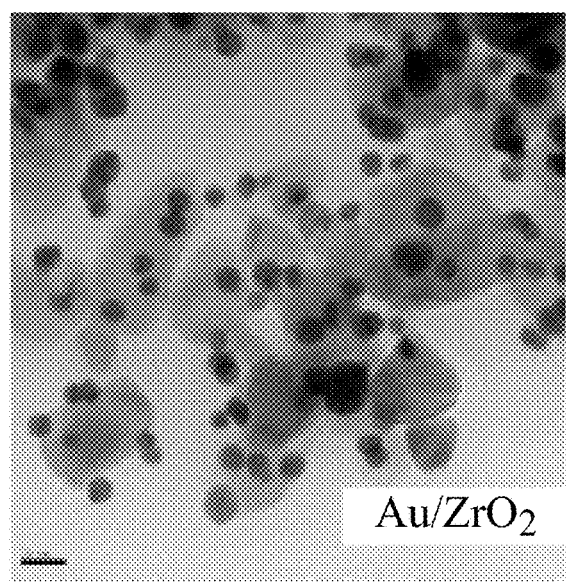

FIG. 11 shows a TEM micrograph of Au/ZnO and Au/ZrO2. Referring to FIG. 10, the Au particles were uniformly deposited onto metal oxide surfaces, and the deposited Au particles size was 5-20 nm.

Figure 12:
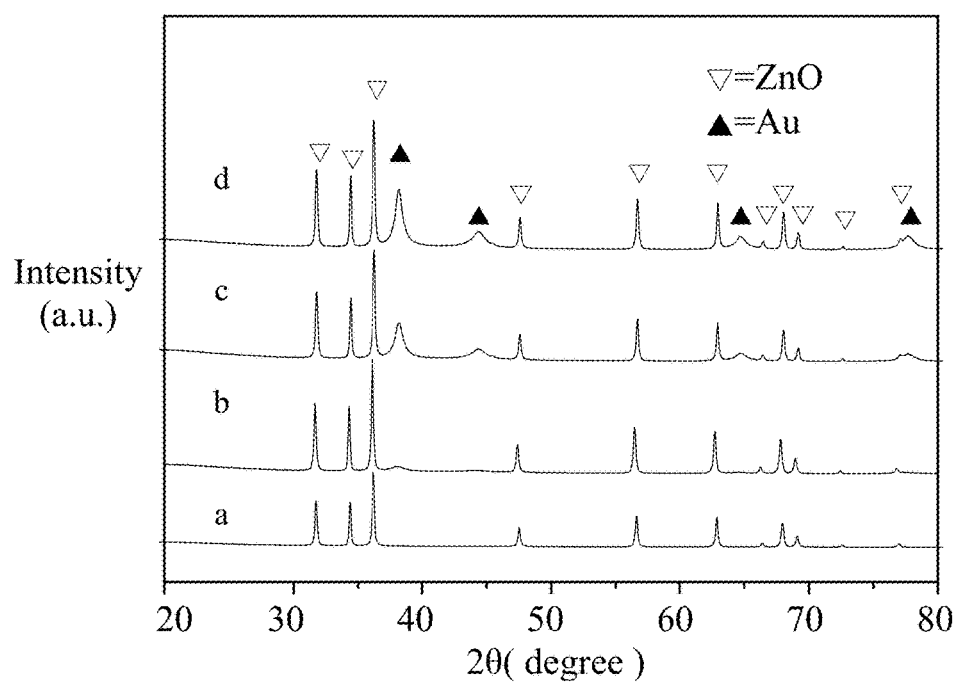
FIG. 12 shows X-ray diffraction of ZnO and Au/ZnO particles.

FIG. 12 shows XRD analysis of Au/ZnO, wherein the (a) line represents pure ZnO, and (b), (c), and (d) lines represent Au/ZnO at X-ray exposure times of 1 minute, 3 minutes, and 10 minutes, respectively.

Comparative Example 1

In Comparative Example 1, the X-Ray exposure experiments were conducted at two additional X-Ray sources: (1) in house X-Ray diffractometer (Photon energy of 8 KeV); and (2) Synchrotron X-Ray at BL 17C1 with a photon energy of 11.919 KeV (matching Au $L_3$ edge). The criteria to judge whether the gold ions had been reduced to zero-valence gold was by examining the color change of the solution after exposure. The hydrogen tetrachloroaurate solution with the same composition as for white synchrotron X-Rays were contained either in a plastic plate (For in house X-Ray machine) or capsulated within a plastic bag (for Synchrotron X-Ray). After 2-3 hours of exposure, the solution color didn't change. The results indicated that both X-Rays sources are incapable for producing gold particles in solutions due to their low intensity of X-Rays.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method for preparing particles, comprising:
   providing a precursor solution containing a precursor dissolved in a solution comprising water, ethanol, or a combination thereof, wherein the precursor comprises silver nitrate, chloroauric acid, ferrous chloride, nickel sulfate, copper sulfate, or zinc chloride;
   adding a polyethylene glycol, a poly(etherimide), or a poly(vinyl pyrrolidone) to the precursor solution, wherein no free radical scavenger is present in the precursor solution; and
   irradiating the precursor solution with an ionizing radiation beam having a dose rate of above 7.4 $J/cm^2 sec$ to convert the precursor to the particles, wherein the ionizing radiation beam is an x-ray.

2. The method as claimed in claim 1, wherein the ionizing radiation beam is a synchrotron X-ray.

3. The method as claimed in claim 1, wherein the precursor solution is irradiated by the ionizing radiation beam for less than 30 minutes.

4. The method as claimed in claim 1, wherein the precursor solution is irradiated by the ionizing radiation beam for less than 30 seconds.

5. The method as claimed in claim 1, wherein the precursor solution is irradiated by the ionizing radiation beam for less than 1 second.

6. The method as claimed in claim 1, wherein the precursor has a concentration of about 0.5 to 2 mM in the precursor solution.

7. The method as claimed in claim 1, wherein the precursor solution has a pH value of about 4 to 10.

8. The method as claimed in claim 7, wherein the precursor solution further comprises a granular structure, and the particle is formed on a surface of the granular structure.

9. The method as claimed in claim 8, wherein the granular structure comprises phosphorus, gold, silver, titanium oxide, zinc oxide, or zirconium oxide.

* * * * *